US006440441B1

(12) United States Patent
Hicks et al.

(10) Patent No.: US 6,440,441 B1
(45) Date of Patent: *Aug. 27, 2002

(54) **METHOD FOR CONTROLLING *SPHAEROTHECA PANNOSA* INFECTIONS OF ROSE PLANTS USING WAX ESTERS**

(75) Inventors: Scott C. Hicks; Sidney R. Siemer, both of Fresno, CA (US)

(73) Assignee: IJO Products, LLC, Fresno, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/316,152

(22) Filed: May 21, 1999

(51) Int. Cl.$^7$ .................................................. A01N 25/02
(52) U.S. Cl. ........................ 424/406; 424/405; 424/776; 424/195.1; 514/506; 514/552; 514/549; 514/937
(58) Field of Search .................. 424/405, 406, 424/776, 195.1; 514/506, 529, 546, 549, 552; 504/114, 117

(56) References Cited

U.S. PATENT DOCUMENTS

| | | | |
|---|---|---|---|
| 3,983,214 A | | 9/1976 | Misato et al. |
| 4,002,775 A | | 1/1977 | Kabara |
| 4,771,571 A | | 9/1988 | Obrero et al. |
| 5,366,995 A | | 11/1994 | Savage et al. |
| 6,174,920 B1 | * | 1/2001 | Hicks et al. ................ 514/549 |

OTHER PUBLICATIONS

Abd–Aziz et a., Jojoba Leaf Extracts: Potential as Antimicrobial and Antinematode Agents, Proceedings of the Ninth International Conference on Jojoba and its Uses, Catamarca, Argentina, pp 145–149, Sep. 25–30 (1994).

Sohby et al., Some Biological and Pharmaceutical Studies on Jojoba Oil, Bull. Fac. Pharm., Cairo Univ., vol. 34, No. 3, pp. 239–243 (1996).

Young, Roderick, Jojoba Wax Protective Spray, Canadian Patent Application No. 2,103,014 (Abandoned), published May 13, 1995.

Committee on Jojoba Utilization, Products From Jojoba: A Promising New Crop for Arid Lands, National Academy of Sciences, (1975).

Wisniak, Jaime, Jojoba Oil and Derivatives, Prog. Chem. Fats other Lipids, vol. 15, 167–218 (1977).

Frick, et al., Eradication of Apple Powdery Mildew From Infected Buds, Plant Disease Reporter, Vo. 56, No. 9, (Sep. 1972).

Kabara, John J., Antimicrobial Agents Derived from Fatty Acids, JAOCS, vol. 61, No. 2, (Feb. 1984).

* cited by examiner

*Primary Examiner*—Neil S. Levy
(74) *Attorney, Agent, or Firm*—Townsend and Townsend and Crew

(57) ABSTRACT

A new method of preventing and eradicating *Sphaerotheca pannossa* (powdery mildew) infections on rose plants using a wax ester emulsion is provided wherein the wax esters emulsion is comprised of wax esters, which are derived from esterification of monoethylenic acids and monoethylenic alcohols having between 18 and 24 carbons, and a surfactant at a concentration of between 1% v/v and 7%v/v of the total wax ester component.

5 Claims, No Drawings

METHOD FOR CONTROLLING *SPHAEROTHECA PANNOSA* INFECTIONS OF ROSE PLANTS USING WAX ESTERS

FIELD OF THE INVENTION

This invention relates to a method of controlling *Sphaerotheca pannossa* (powdery mildew) infection of rose plant by the application of a fungicidal wax ester emulsion, wherein the wax esters are the esterification product of monoethylenic acids and monoethylenic alcohols having between 18 to 24 carbons each and are emulsified in water with surfactants. Preferably, the wax esters are comprised of a mixture of wax esters which are at least 85% identical to the type and concentration of wax ester found in naturally occurring jojoba extract, with a surfactant at a concentration between 1% v/v and 10% v/v of the total wax ester mixture.

BACKGROUND OF THE INVENTION

Over the last thirty years it has been a goal of various government agencies to develop uses for the desert plant jojoba (*Simmondsia chinensis*), especially the extract produced from the jojoba seeds. Due to the jojoba plant's ability to thrive in arid climatic conditions in coarse desert soils and it's life span which can extend up to 200 years, the plant was thought to be particularly useful for developing an agricultural industry in the underutilized lands of the American southwest.

The jojoba plant produces an abundance of seeds with an average yield for a mature plant of about 12 pounds (dry weight). Jojoba seeds contain about 50% by weight of a colorless, odorless oily extract which is commonly referred to as "jojoba oil". The extract is chemically an unsaturated wax made up of non-glyceride esters having a narrow range of chemical composition. Another natural source for wax esters is spermaceti, a wax produced from the head of the sperm whale. As the sperm whale is an endangered species and interstate sale of its oil was banned in 1973, it is not recognized as a particularly useful source for these wax esters.

Jojoba oil is more than 97% wax esters. Each wax ester is derived from one molecule of a long-chain monoethylenic alcohol esterified with one long-chain monoethylenic fatty acid. The wax esters typically are comprised of carbon chains of 38 to 44 carbon atoms. Suprisingly, the wax ester components of jojoba oil have been found to exhibit superior fungicidal capabilities.

Powdery mildew is the common name applied to one of the most damaging and wide spread diseases in the agricultural and horticultural industry. Powdery mildew is a disease caused by species of several genera of fungus on a number of different host plants. The variety of horticultural and agricultural plants susceptible to powdery mildew disease is large. The disease is called "powdery mildew" because of appearance of the mycelial growth gives a powder like appearance on the surface of the host. The white powdery growth appears on infected leaves, stems, fruit and flower buds. Infected leaves may also appear distorted and fall from the plant. Powdery mildew spores are easily spread by wind to nearby plant tissue and to other plants, resulting in an epidemic if left unchecked.

*Sphaerotheca pannossa* is the fungus species which causes powdery mildew infection on rose plants. Powdery mildew infection is prevelent problem in the rose crop industry. This is particularly problematic since this crop value depends on its appearance. In fact, *Sphaerotheca pannossa* infection is known to cause millions of dollars in rose crop damage per annum.

Various chemical compounds have been disclosed which claim suitability for use as a fungicide for controlling powdery mildew infection. For example, U.S. Pat. No. 5,366,995 discloses the use of short chain fatty acids and their salts as a fungicidal agent. The disclosed fatty acids generally have carbon chains of between 7 to 20 carbon atoms and preferably at 18 carbons. None of these application disclose the high molecular weight wax esters commonly found in jojoba extract for use as a fungicidal agent. Further, jojoba extract has been reported as a pretreatment to prevent powdery mildew infection on grape plants (Canadian Patent Application No. 2,103,014). In contrast, the subject invention is directed towards the use of wax esters for prevention and eradication of *Sphaerotheca pannossa* infection of rose plants.

In our studies, it has been surprisingly determined that the wax esters found in jojoba extract are both an inert physical barrier and an eradicant of *Sphaerotheca pannossa*. This discovery gives rise to commercially important applications.

In modern agriculture and horticulture the avoidance of unnecessary environmental loading is a key commercial advantage. Both horticulture oils and fungicides are applied repeatedly during the early stages of the growing season to prevent the powdery mildew infection from becoming established. The oils and fungicides are applied multiple times per growth cycle to prevent powdery mildew infection and then again if powdery mildew appears. Since many crops have two or more growing cycles per year, this leads to yet more fungicidal treatments. As a result, the frequent fungicidal applications lead to a build up of that particular chemical agent in the environment (environmental loading).

Conversely, application of the wax esters of the subject invention can be limited to instances where a powdery mildew infection occurs. Thus, wax ester fungicidal treatments are limited to a few, if any, application per growing season and environmental loading is significantly lowered. Less fungicidal applications also results in a lower cost to growers. In addition, the wax ester fungicidal agent is rainfast after the application has dried. Thus, the wax ester fungicidal agent can prevent *Sphaerotheca pannossa* from infecting a rose plant in a single application but also kills existing infections and then prevents reinfection over time. Jojoba extract has the ability to eradicate *Sphaerotheca pannossa* tolerant or resistant strains that have evolved under current fungicidal protocols. Therefore, use of a jojoba extract as a fungicide is economically efficient and significantly reduces environmental loading.

The wax esters provide a greater degree of safety than horticultural oils and fungicides. Many of the existing horticultural oils and fungicides are generally not environmentally safe in their application. For example, use of petroleum oils and sulfuric fungicidal applications for powdery mildew are restrained under the federal regulations as they have serious environmental ramifications if applied in a concentrated form or in high volume. Further, the fungicides and oils are generally volatile. Thus, use of these materials is hazardous to workers applying the chemical. Another popular fungicide, sterol inhibitors, are also heavily regulated because of their environmental impact and the residues they leave on edible crops. The wax esters used in this invention provide particular stability and are significantly less volatile than horticultural oils. Specifically, the greater degree of unsaturation and the long carbon chains, which are almost twice as long as fatty acid oils, enhances stability and non-volatility. Jojoba extract is a safe and natural application and is not heavily impacted by regulatory laws.

Additionally the wax esters of the subject invention have other advantages which make them a particularly effective as a fungicidal agent for treatment of *Sphaerotheca pannossa* infection in rose plants. For example, the long chained wax esters are generally non-toxic for predator, beneficials and honeybees. The wax ester agent is generally non-phytotoxic at the preferred range of use and, unlike many of the prior art fungicides mentioned above, never "burn" plant tissue. In fact the wax esters have been found to promote photosynthesis and stomatal conductance in the host plant.

SUMMARY OF THE INVENTION

It has been discovered that wax esters having high molecular weight are a particularly effective and safe fungicidal application for preventing and eradicating *Sphaerotheca pannossa* infections on rose plants. This invention provides a method for treating rose plants infected with powdery mildew fungus with an emulsion of wax esters comprising wax esters of between 36 to 44 carbon atoms and a surfactant. The wax esters are derived from the esterification of monoethylenic acids and monoethylenic alcohols having between 18 and 24 carbons and the surfactant at a concentration of between 1% v/v and 10%v/v of the total wax esters composition.

Thus, in a preferred embodiment the invention provides a method of preventing and eradicating *Sphaerotheca pannossa* infection on a rose plant wherein the method comprises spraying an aqueous emulsion of a wax esters with a surfactant onto the rose plant in an amount sufficient to reduce fungal infection in sprayed plants by at least 10% when compared to plants not sprayed with wax esters and wherein at least 50% of the wax ester is comprised of carbon chains of 36 to 44 carbons atoms.

In another preferred embodiment of the present invention, the wax esters are derived from the esterification of monoethylenic acids and monoethylenic alcohols. The monoethylenic acids are chosen from a range of 18 to 22 length carbon chains and the monoethylenic alcohols from a range of 20 to 24 length carbon chains.

In another preferred embodiment of the present invention, 50% to 90% of the wax esters are a mixture of eicosenyl eicosenoate and docosenyl eicosenoate.

In yet another preferred embodiment of the present invention, the wax esters are comprised of a mixture of wax esters which are 85% similar in type and concentration to the wax ester found in naturally occurring jojoba extract.

In yet another preferred embodiment of the present invention the fungicidal agent is jojoba extract in an aqueous emulsion, with a suitable surfactant.

DEFINITIONS

The term "emulsion," as used herein refers to a stable mixture of two or more immiscible liquids held in liquid suspension. The mixture may be stabilized by the presence of emulsifiers or surfactants.

The term "aqueous emulsion," as used herein refers to preparations of a wax or oil distributed in small globules throughout the body of a second liquid which is water. When the dispersed liquid is an oil or wax and is in the discontinuous phase and the dispersion medium is in the continuous phase it is an oil in water emulsion, whereas when water or aqueous solution is the dispersed phase and oil, wax or is the continuous phase, it is known as a water in oil emulsion.

The term "surfactants," as used herein refers to emulsifiers, detergents, surface active agents, anti-foaming agents or compounds which reduce surface tension when dissolved in water of a water solution, or which reduce interfacial tensions between two liquids. Thus the surfactant changes the properties of a solvent so that immiscible liquids may be more easily stabilized. Fundamentally, a surfactant is a single molecule comprised of two structurally dissimilar groups of opposing solubility tendencies, one which has an affinity for the phase and the other which is antipathic to the medium. The surfactant causes adsorption at the solution's interfaces, orientates the adsorped surfactant ions or molecules , promotes micelle formation in the bulk of the solution, and orientates the surfactant ions or molecules in the micelle, thereby increasing the solubility of the solvent and stabilizing the mixture.

The term "wax esters," as used herein refers to esters of long chain, even-numbered fatty acids and monohydric, straight chain, aliphatic alcohols, or sterols. Waxes are usually ester mixtures often accompanied by small percentages of free fatty acids or high molecular weight unbranched hydrocarbons. The wax acids and wax alcohols usually have a similar number of carbon atoms and are very hydrophobic.

The term "monoethylenic acids," as referred herein refers to carboxylic acid organic compounds where the carboxyl group is attached to one end of a hydrocarbon and the hydrocarbon contains a single double bond.

The term "monoethylenic alcohols," as referred herein refers to organic compounds where one or more hydroxyl groups (OH) are present in a hydrocarbon molecule with no more than one hydroxyl group attached to a single carbon atom and which also includes a single double bond in the hydrocarbon molecule.

The term "non-ionic surfactants," as referred to herein refers to surfactants, detergents or emulsifiers which do not ionize in water and thus are not subject to hydrolysis by aqueous solutions of acid or alkali.

The term "siloxanes," as referred to herein refers to straight chain compounds consisting of silicon atoms single-bonded to oxygen and arranged so that each silicon atom is linked with four oxygen atoms. In some cases, hydrogen may replace two or more of the oxygens.

The term "polysiloxanes," as referred herein refers to siloxane chains wherein some of the oxygens are replaced with organic substituents so that a linear polymer results.

DETAILED DESCRIPTION

Introduction

Fungicidal infection in the rose crop industry represents a significant loss for rose growers in that fungal growth on crops may inhibit production of foliage and lower the lower overall quality of cultivated roses. *Sphaerotheca pannossa* infection of rose plants is one of the most commonplace and damaging of such fungus. Current treatments for *Sphaerotheca pannossa* have damaging environmental side effects, are not particularly effective and in some cases are damaging to the rose plant itself.

It has recently been found that long chain wax esters have special utility as a fungicidal agent for *Sphaerotheca pannossa* infection on rose plants. Particularly, aqueous emulsions of wax esters with a suitable surfactant, wherein the wax esters are the esterification product of monoethylenic acids of between 18 and 22 carbon chains and monoethylenic alcohols of between 20 to 24 carbon chains, are useful as fungicidal agent for *Sphaerotheca pannossa* infection on rose plants This invention provides methods of use for wax esters as a fungicidal agents for the treatment and prevention of powdery mildew infection on rose plants.

Wax Ester Sources

The wax esters of this invention are most conveniently extracted from *Simmondsia chinensis* (Jojoba). *S. Chinensis* is grown commercially for its wax esters. However, this invention is not intended to be limited by the origin of the wax esters of either synthetically or biologically origin. Sexual crosses between species is the genus. Related species in the genus are expected to yield novel plants which produce the wax esters for use in this invention.

Jojoba extract is more than 97% wax esters. Wax esters are derived from one molecule of a long-chain alcohol esterified with one long-chain fatty acid. Jojoba oil contains no glycerides, very little (1 percent) free acid or alcohol, and almost no hydrocarbons, steroids or other contaminants. Carbon chains of 18 and 24 atoms long make up about 93% of the acids and alcohols in the wax esters.

The unsaturated acid components of jojoba's wax esters are mostly a mixture of eicosanoic ($C_{20}$), docosanoic ($C_{22}$) and octadecanoic ($C_{18}$) acids. The unsaturated alcohols are a mixture of eicosanol and docosanol, with smaller quantities of tetracosanol ($C_{24}$) and alcohols of lower molecular weight. Over 85% of the esters present in jojoba oil are combinations of $C_{20}$ and $C_{22}$ acids and alcohols. The double bond position on the acids and alcohols typically falls between carbon 11 and carbon 12, and between carbon 13 and carbon 14.

More accurately, the alcohol content is comprised of 43.8% Eicos-11-enol, 44.9% Docos-13 enol and 8.9% Tetracos-15-enol ($C_{24}$). The acid content consists of 71.3% Eicos-11-enoic acid, 13.6% Docos-13-enoic acid and 10.1% Octdec-9-enoic acid. Percentage's of composition components at or below 2% are defined as trace components and are not included in this description.

Further, the wax esters present in jojoba oil typically break down to 30.9% Eicosenyl Eicosenoate ($C_{40}$), 43.2% Docosenyl Eicosenoate ($C_{42}$), 7.6% Eicosenyl Docosenoate ($C_{42}$), 6.2% Tetracosenyl Eicosenoate (C44) and 5.9% Eicosenyl Octadecenoate ($C_{38}$). Percentage's of components below 2% were defined as trace components and not included in the above description.

Extraction of Wax Esters from Natural Sources

The extraction of wax esters from jojoba can be carried out by any standard technique as is used in the industry for the extraction of fats or waxes from seeds, beans or nuts. For example, crushing or pressing the seeds and collecting the wax is one such technique. Other techniques contemplated may be the use of solvents to extract the wax. Solvents such as benzene, hexane, heptane and carbon tetrachloride have been shown to readily extract the desired wax esters in a satisfactory yield without special difficulty or affecting properties of the wax.esters.

Synthesis of Wax Esters

Although it is preferable to extract the wax esters for the subject invention from naturally occurring sources such as jojoba plant, wax esters of this invention can be synthesized by a variety of standard esterification methods as is known in the art (see March, J., "Advanced Organic Chemistry—Reactions, Mechanisms, and Structures", $4^{th}$ ed., (1992)). For example, an acid catalyzed esterification of carboxylic acids with alcohols ( the Fischer esterification reaction), wherein equilibrium is driven to the right, is one such esterification technique. Techniques commonly used to drive this reaction to the right include adding an excess of reactant (usually the alcohol), removal of the ester or water product by distillation, or removal of the water product by azeotropic distillation, use of a dehydrating agent or a molecular sieve. One skilled in the art would appreciate that this is just one of several esterification reactions available to the synthesize the wax esters contemplated in this invention.

As described above, the esterification reactions would be carried out with monoethylenic acid and alcohol precursors comprising carbon chains from about 18 to 24 carbon atoms, which are commonly sold by a variety of vendors. For the purposes of illustration, purchasing 13-docosaenoic acid and 11-eicosenol from Sigma-Aldrich Fine Chemicals Co. (see Sigma Catalog for Biochemicals and Reagents for Life Sciences, pg. 417 and 407 respectively, (1999)), combining these two precursors with an acid catalyst such as $H_2SO_4$ or TsOH while drawing off the product ester or water by distillation would give the wax ester docosenol eicosenoate, a wax ester whose use as a fungicidal agent is detailed in this invention.

Application of Wax Ester Fungicidal Agents

The wax ester fungicidal agent may be applied to a variety of rose plants including bushes, vines, miniatures or hybrids. Specifically, the subject invention is contemplated to be used on any rose plant of the genus Rosa. For example, the subject wax ester fungicidal agent is particularly well suited for preventing or eradicating *Sphaerotheca pannossa* (powdery mildew) infections for florabunda, grandiflora, hybrid tea, miniature or bush rose species. More particularly, the subject wax ester fungicide is an effective preventative and eradicant of *Sphaerotheca pannossa* var. *rosa*. One skilled in the art will appreciate the vast number of rose plant species and varieties which exist and that efforts to breed new species and varieties are currently underway. Thus, other species of rose plants which may be treated by the subject invention would be obvious to any person skilled in the art.

The wax ester fungicidal agent of this invention may be formulated into various forms such as solution, wettable powder, emulsion or spray, by mixing with any suitable solid or carrier such as water. It is preferred that the wax ester application is applied in the form of an aqueous emulsion and such emulsions may also comprise a surfactant or combination of surfactants.

The wax ester formulation may be applied by any of the methods typically known and used in the agricultural industry for the application of a chemical. Preferably, the wax ester composition would be applied by any common spraying technique, including crop dusting by airplane or vehicle. However, the most preferable method for application of the subject wax ester fungicidal agent is by any ground or hand sprayer which is commonly used in the agricultural industry. The wax ester emulsion is sprayed over the entire plant just to the point of runoff. Alternatively, specific points of infection may be treated directly without effecting other parts of the rose plant. That is, a single bunch of leaves or flowers on a rose plant may be sprayed with care given not to apply the wax ester emulsion over the whole of the plant.

The surfactants which can be employed in the wax ester fungicidal agent can be any of the non-phytotoxic surfactants which are customarily used in preparing agricultural formulations. The surfactant would be one which adequately increases the solubility of the wax ester in water and which stabilizes the mixture by increasing break time so that the wax ester emulsion stays in the emulsified state long enough to be applied over a large acreage. Further, a surfactant should be chosen which increase the spreadability of the wax ester composition, so that the wax ester solution spreads at the same rate as the water phase over the various treated surface. In this way a filmy, uniform and rainfast application of the wax esters is achieved. Specifically, it is preferred for the present invention that the wax esters be mixed with a non-ionic surfactant, a siloxane or a polysiloxane. Surprisingly, it was found that the optimal composition was one where the wax esters were mixed with a non-ionic detergent to increase solution stability and then with a polysiloxane to enhance spreadability. Thus, the most preferred composition is one in which a combination of surfactants are employed. These type of surfactants and their use are well known in the art. A preferable non-ionizable surfactant would be IGEPAL CO[nonylphenoxypoly (ethyleneoxy)ethanol] or IGEPAL CA[octyphenoxypoly (ethyleneoxy)ethanol], manufactured by Rhone-Poulenc. Additionally, a preferable polysiloxane surfactants would be a polyether-polymethylsiloxane-copolymer such as Break-Thru® OE 441, a polysiloxane manufactured by Goldschmidt Chemical Corporation.

The wax ester fungicidal agent of the present invention can be diluted in order to facilitate its application in the field. Preferably, the wax ester/ surfactant mixture would be diluted in water to form an aqueous emulsion and sprayed over the plant. The dilution should be at a concentration to maximize fungicidal activities without injuring the plant. It is preferred that the wax ester /surfactant mixture be diluted from 0.25% v/v to about 5% v/v in water for optimum fungus eradicating and prevention activity. For example, a 0.25% to 0.5% emulsion would be produced by mixing 1–2 pints of the wax ester/surfactant composition with approximately 40 to 50 gallons of water, for treatment of approximately one acre of the rose crop land. One skilled in the art would appreciate that the stated volume of wax ester fungicide for treatment of one acre represents an application for intermediate foliage. The volume would be increased when the foliage of the treated rose plants abundant and mature, and decreased when the foliage is relatively sparse and new.

In addition to large scale applications for farms, greenhouse and agribusiness crop lands, the wax ester fungicidal agent can be employed as a preventative and eradicator of *Sphaerotheca pannossa* for home and garden rose plants. Thus, it is contemplated that the wax ester agent is also used in a ready-to-use formulation for home use. The preferred concentrations of wax ester to surfactant to water is consistent as to what has been described herein. Preferably, the ready-to-use formulation would be 5% wax ester, 3.5% non-ionic surfactant and 3.5% siloxane or polysiloxane surfactant, all of which is diluted in water to form an 12% wax ester/surfactant concentration in water. In addition, a non-diluted wax ester/surfactant preparation of the same proportions above may be formulated as a refill product, where the refill product will later be diluted at the home by approximately 1 ounce of wax ester/surfactant to 1 quart of water.

Those skilled in the art will appreciate that the time of application of the wax ester fungicidal agent is determined by the particular characteristics and environment of the rose species to be treated. Generally, the wax ester fungicidal agent can be applied at any time in the growth cycle. Preferably, the wax esters are applied to the rose plant early in the growing season, most preferably on growth tips or young plant tissue, to prevent the infection from being established. This is particularly true where there has been prior infection in the previous growing season since powdery mildew will overwinter inside stems and bud scales. Thus, application of the wax ester fungicide may be made as early as just before the first buds swell. It is also preferable the wax esters are applied at the first sight of the powdery mildew infection. In that way the infection may be eradicated before it spreads to other plants. Further, the wax ester residue is rainfast and will coat the treated plant surface for some time, thus preventing reinfection.

The wax esters of the subject invention exhibit excellent fruit thinning abilities. Therefore, application of the wax ester composition as a fungicidal agent is best made after anthesis. However, the subject wax ester fungicidal agent may be applied at the flowering stage of the rose plant but greater care would have to be made to ensure that the wax esters are not applied to the fruiting body. Additionally, if a powdery mildew infection exists at the time of harvest, application of the wax ester fungicidal agent can still effectively be made.

Optionally, this invention is to be used at a time when ambient temperature is not conducive to white fly infestation. White fly infestation is associated with high heat and moisture, in a range from 80° F. to 100° F., and most commonly between 85° F. to 95° F. In contrast, powdery mildew is a disease associated with relatively cool temperatures. Thus, the application of wax esters for control of powdery mildew is made when temperature is below 80° F., and preferably between 55° F. to 65° F. when powdery mildew first begins to appear.

While a single application of the wax ester fungicidal agent should be satisfactory for effective *Sphaerotheca pannossa* eradication, the wax ester fungicidal agent may be applied multiple times to achieve the desired effect. However, in applications wherein the wax ester composition make up more than 2.5% of the aqueous solution by volume, a subsequent application cannot be applied for at least 10 days have elapsed. or host injury may occur. Further, applications at or above 5% wax ester emulsion may result in an phytoxic effect on the leaves.

EXAMPLES

The following examples are offered to illustrate, but not to limit the claimed invention.

Example 1 details a wax ester fruit thinning formulations.

Example 2 illustrates the fungicidal ability to eradicate and prevent *Sphaerotheca pannossa* infection on rose plants of aqueous emulsions wax esters.

Example 1

Example 1 provides a preparation of a wax ester and surfactant composition diluted water to form an aqueous emulsion for use as a fungicidal agent. Specifically, herein is provided the preparation of a composition of wax esters which resemble in type and concentration the wax esters found in jojoba extract by at least 85%, with a combination of surfactants to increase stability and spreadability of the wax ester solution, in an aqueous emulsion.

A solution containing 93% v/v of a wax ester mixture comprising 43% docosenyl ecosenoate, 30% eicosenyl eicosenoate, 7.5% eicosenyl eicosenoate, 6% tetracosenyl eicosenoate and 5% eicosenyl octadecenoate, with a 7% mixture of surfactants was prepared. The solution was prepared by mixing together 93% jojoba extract v/v with 3%v/v a non-ionic type surfactant and 4% polysiloxane type surfactant. The non-ionic surfactant was Igepal CA-520 from Rhone-Poulenc, which is an octylphenol ethoxylate containing 5 moles by weight of ethylene oxide. The polysiloxane used was Break-Thru® OE-441 from Goldschmidt Chemical Corporation, which is a polyether-polymethylsiloxane-copolymer. The wax ester and surfactant composition was mixed for 20 minutes by return flow agitation. The resultant solution contained the wax esters at the desired stability and spreadability to effectively destroy powdery mildew fungus infection over a rose plant surface. The wax ester solution can then be diluted in water to form an aqueous emulsion for application to rose plant.

Example 2

Example 2 demonstrates an aqueous emulsion of wax esters application for eradicating *Sphaerotheca pannossa* (powdery mildew) infection on rose plants.

The wax ester fungicideal agent was prepared according to Example 1 at concentrations of 0.5%, 1%, 2.5% and 5% (by volume) diluted in water. The wax ester emulsion was applied onto separate potted plants of the Tyler variety, hybrid Tea rose plants. The effect of the wax ester emulsion was compared to untreated trees to establish the fungicidal capability of the wax esters. The wax ester was applied by handsprayer to runoff over the whole of the rose plant. Three replications of the experiment were completed.

Data was gathered at 6 days after the first application and the again 8 days after all 4 treatments were applied. On those days, evaluation consisted of rating plant tissue including foliage, flower buds, flower stems and flowers for both the percentage incidence of fungal infection over the plant and the severity of infection at those points of infection. Table 1 summarizes the percentage powdery mildew infection reduction data for the unsaturated wax ester treatment versus untreated plants.

TABLE 1

| | Average Powdery Mildew Infection (%) | | | | | |
|---|---|---|---|---|---|---|
| | Pre-treatment | | 6 Days After 1 Appln. | | 8 days after 4 Applns. | |
| Formulation (% v/v) | Incidence | Severity | Incidence | Severity | Incidence | Severity |
| Untreated | 25% | 27% | 28% | 33% | 26% | 22% |
| .5% Wax Ester | 22% | 23% | 10% | 10% | 0.0% | 0.0% |
| 1% Wax Ester | 25% | 28% | 10% | 10% | 0.0% | 0.0% |
| 2.5% Wax Ester | 22% | 25% | 13% | 20% | 0.0% | 0.0% |
| 5% Wax Ester | 28% | 25% | 17% | 23% | 0.0% | 0.0% |

It was found that a wax ester fungicidal agent applied in an aqueous emulsion effectively destroyed *Sphaerotheca pannossa* infections both after a single application and, to a greater extent, with multiple applications. That is, a marked decrease in powdery mildew infection was observed after a single treatment and complete eradication was achieved after 4 applications. Further, the plants did not exhibit a reinfection of *Sphaerotheca pannossa* despite the presence of the infected but untreated rose plants, which were still in close proximity to the treated plants.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for controlling an *Sphaerotheca pannossa* infection on a rose plant, said method comprising:

spraying an aqueous emulsion of a wax ester, or mixture of wax esters, with a surfactant onto the growth tips of the rose plant, said emulsion in an amount sufficient to reduce fungal infection in the treated rose plants by at least 10% of the amount in absence of said wax ester, wherein the wax ester is derived from jojoba extract, wherein the weight ratio of surfactant to wax ester is from 1:10 to about 1:50 and wherein the emulsion is between about 0.25% to about 7% v/v wax esters and surfactant.

2. The method of claim 1 wherein the rose plant is a hybrid.

3. The method of claim 1 wherein the rose plant is chosen from grandiflora, florabunda, bush, miniature or tea rose plants.

4. The method of claim 1 wherein the emulsion further comprises a surfactant, or combination of surfactants selected from a group consisting of: ethoxylated alkyl phenyl ethers, siloxanes and polysiloxanes.

5. The method of claim 1 wherein about 50% to about 90% of the wax ester is a mixture of eicosenyl eicosenoate and docosenyl eicosenoate.

* * * * *